(12) United States Patent
Kayyali et al.

(10) Patent No.: US 9,492,105 B1
(45) Date of Patent: Nov. 15, 2016

(54) DEVICE FOR SLEEP DIAGNOSIS

(75) Inventors: Hani Kayyali, Shaker Heights, OH (US); Matthew Tarler, Westlake, OH (US); Edward J. Rapp, Cleveland Heights, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 1700 days.

(21) Appl. No.: 12/370,996

(22) Filed: Feb. 13, 2009

(51) Int. Cl.
| | | |
|---|---|---|
| A61B 5/00 | (2006.01) | |
| A61B 5/08 | (2006.01) | |
| A61B 5/087 | (2006.01) | |
| A61B 5/113 | (2006.01) | |
| A61B 5/0205 | (2006.01) | |
| A61B 5/0432 | (2006.01) | |

(52) U.S. Cl.
CPC ............... *A61B 5/08* (2013.01); *A61B 5/0806* (2013.01); *A61B 5/087* (2013.01); *A61B 5/113* (2013.01); *A61B 5/02055* (2013.01); *A61B 5/04325* (2013.01); *A61B 5/0816* (2013.01); *A61B 5/6801* (2013.01); *A61B 5/6831* (2013.01); *A61B 2562/221* (2013.01)

(58) Field of Classification Search
USPC .................................. 600/300–301, 534–536
See application file for complete search history.

(56) References Cited

U.S. PATENT DOCUMENTS

| | | | |
|---|---|---|---|
| 4,308,872 A | | 1/1982 | Watson et al. |
| 4,807,640 A | * | 2/1989 | Watson et al. ................. 600/534 |
| 4,817,625 A | | 4/1989 | Miles |
| 4,889,131 A | | 12/1989 | Salem et al. |
| 5,295,490 A | * | 3/1994 | Dodakian ..................... 600/534 |
| 5,454,376 A | * | 10/1995 | Stephens et al. ............. 600/534 |
| 5,483,969 A | | 1/1996 | Testerman et al. |
| 5,685,303 A | * | 11/1997 | Rollman et al. .............. 600/390 |
| 6,306,088 B1 | * | 10/2001 | Krausman et al. ........... 600/301 |
| 6,425,861 B1 | * | 7/2002 | Haberland et al. ........... 600/300 |
| 6,461,307 B1 | | 10/2002 | Kristbjarnarson et al. |
| 7,081,095 B2 | * | 7/2006 | Lynn et al. ................... 600/538 |
| 7,297,119 B2 | * | 11/2007 | Westbrook et al. .......... 600/529 |
| 7,578,793 B2 | * | 8/2009 | Todros et al. ................ 600/484 |
| 7,593,767 B1 | * | 9/2009 | Modarres ............... A61B 5/048 |
| | | | 600/529 |
| 7,962,098 B2 | * | 6/2011 | Kimoto et al. .............. 455/41.2 |
| 8,172,766 B1 | * | 5/2012 | Kayyali et al. ............... 600/534 |
| 2002/0032386 A1 | * | 3/2002 | Sackner et al. .............. 600/536 |
| 2003/0100843 A1 | * | 5/2003 | Hoffman .............. A61B 5/0809 |
| | | | 600/538 |
| 2004/0225227 A1 | * | 11/2004 | Newman ............. A61B 5/1135 |
| | | | 600/534 |
| 2005/0144706 A1 | * | 7/2005 | Taylor et al. ..................... 2/338 |
| 2005/0261559 A1 | * | 11/2005 | Mumford et al. ............ 600/300 |
| 2006/0255955 A1 | * | 11/2006 | O'Connor et al. ......... 340/573.1 |
| 2006/0258948 A1 | | 11/2006 | Linville |

(Continued)

*Primary Examiner* — William Thomson
*Assistant Examiner* — Bobby Soriano
(74) *Attorney, Agent, or Firm* — Brian Kolkowski

(57) ABSTRACT

The present invention is related to a compact, portable, user-friendly sleep disorder diagnosis and screening device. The present invention is further related to a single-ended respiratory inductance plethysmography belt used to monitor certain parameters of a subject's respiration while at the same time serving to position and mechanically stabilize a compact data acquisition system about a subject's thorax or abdomen. In one application of the present invention to screen for sleep disorders, the single-ended respiratory inductance plethysmography belt is worn by the subject and a compact data acquisition unit is attached to the belt to which appropriate additional sensors and components such as a pulse oximeter and a nasal cannula are connected. Data is then collected using the belt, compact data acquisition unit, and sensors and is used to determine whether the subject has, or is at risk of having, a sleep disorder.

6 Claims, 4 Drawing Sheets

(56) References Cited

U.S. PATENT DOCUMENTS

| | | | |
|---|---|---|---|
| 2006/0282001 A1* | 12/2006 | Noel et al. | 600/535 |
| 2007/0299325 A1* | 12/2007 | Farrell et al. | 600/301 |
| 2008/0045809 A1* | 2/2008 | Hermannsson | 600/300 |
| 2008/0114220 A1* | 5/2008 | Banet et al. | 600/301 |
| 2008/0119896 A1* | 5/2008 | Wong et al. | 607/2 |
| 2008/0319277 A1* | 12/2008 | Bradley | 600/301 |
| 2009/0024048 A1* | 1/2009 | Lang et al. | 600/534 |
| 2009/0240119 A1* | 9/2009 | Schwaibold et al. | 600/301 |
| 2009/0281394 A1* | 11/2009 | Russell et al. | 600/301 |
| 2009/0318793 A1* | 12/2009 | Datta et al. | 600/391 |
| 2010/0063366 A1* | 3/2010 | Ochs et al. | 600/301 |
| 2010/0204550 A1* | 8/2010 | Heneghan | A61B 5/0205 600/301 |
| 2010/0286546 A1* | 11/2010 | Tobola et al. | 600/534 |
| 2011/0172503 A1* | 7/2011 | Knepper et al. | 600/301 |

* cited by examiner

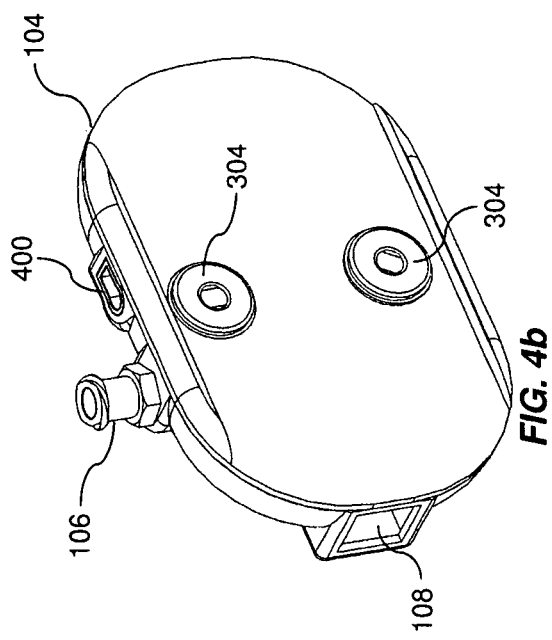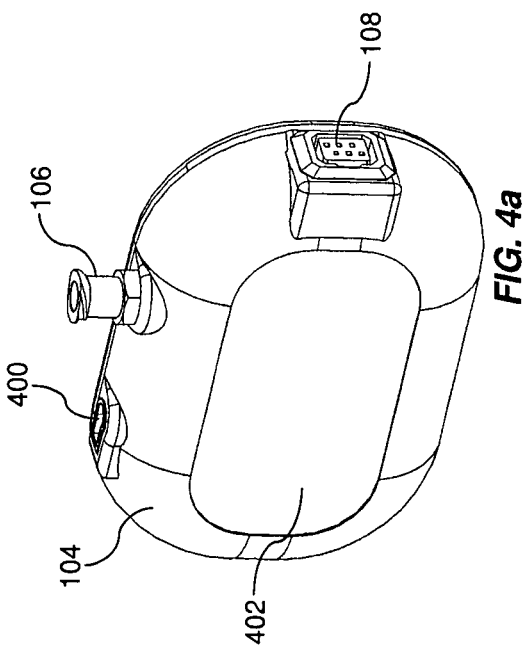
FIG. 4

DEVICE FOR SLEEP DIAGNOSIS

BACKGROUND OF THE INVENTION

1. Field of Use

The present invention is related to a compact, highly portable, user-friendly sleep disorder diagnosis and screening device. The present invention is further related to a respiratory belt to monitor certain parameters of a subject's respiration while at the same time serving to position and mechanically stabilize a compact data acquisition unit about a subject's thorax or abdomen. In one preferred embodiment, the invention comprises a respiratory belt which is placed circumferentially about a subject's thorax or abdomen and to which a compact data acquisition unit capable of recording and/or monitoring at least airflow, respiratory effort and blood oxygen saturation is attached. During use, the respiratory belt is worn by the subject while the subject sleeps and a compact data acquisition unit is attached to the respiratory belt, to which appropriate additional sensors and components such as a pulse oximeter and a nasal cannula are connected. Data is then collected using the device while the subject sleeps and is subsequently used to determine whether the subject has, or is at risk of having, a sleep disorder.

2. Technology Review

Nearly one in seven people in the United States suffer from some type of chronic sleep disorder, and only 50% of people are estimated to get the recommended seven to eight hours of sleep each night. It is further estimated that the medical and social costs associated with sleep deprivation (loss of productivity, industrial accidents, etc.) exceed $150 billion per year. Excessive sleepiness can deteriorate quality of life and is a major cause of morbidity and mortality due to its role in industrial and transportation accidents. Sleepiness further has undesirable effects on motor vehicle operation, employment, higher earning and job promotion opportunities, education, recreation, and personal life.

Primary sleep disorders affect approximately 50 million Americans of all ages and include narcolepsy, restless legs/periodic leg movement, insomnia, and most commonly, obstructive sleep apnea (OSA). OSA's prevalence in society is comparable with diabetes, asthma, and the lifetime risk of colon cancer. OSA is grossly under-diagnosed, with an estimated 80-90% of persons afflicted having not received a clinical diagnosis.

Sleep disorders are currently diagnosed using either simple, subjective methods, various sensor-based objective methods or a combination of the two.

Subjective methods, such as the Epworth and Stanford Sleepiness Scales, generally involve questionnaires that require subjects to answer a series of qualitative questions regarding their sleepiness during various times of the day or while performing various daily activities. With subjective methods such as these, however, it is found that patients usually underestimate their level of sleepiness or they deliberately falsify their responses because of their concern regarding punitive action or as an effort to obtain restricted stimulant medication.

Objective methods of diagnosing sleep disorders generally use a combination of sensors and various physiological measurements to examine a subject's sleep health. One example of such an approach is the use of all-night polysomnography (PSG) to evaluate a subject's sleep architecture. Sleep testing in this manner typically requires measurement of many parameters including brain electrical activity, eye movement, skeletal muscle activity, heart rate, heart rhythm, breathing rate and breathing effort, and blood oxygenation among others. Because of the many sensors used in this approach and the overall complexity of PSG, these tests are typically conducted in a sleep laboratory. While the use of a sleep laboratory and measurement of the many parameters listed above can be advantageous in certain regards, this approach is not without significant drawbacks. Among the difficulties that accompany sleep testing in a sleep laboratory is the fact that a sleep laboratory cannot provide information about a subject's regular sleeping environment. Further, because of the unfamiliar sleeping quarters, the stress of travel to a sleep laboratory, or various other anxieties, many subjects experience "first night effect" when undergoing sleep testing in a sleep laboratory and are unable to properly sleep during testing. Because of this, the first night effect often requires a second night in the sleep laboratory to obtain accurate results for a subject's sleep test leading to greater expense for all parties involved and greater inconvenience to the subject being tested. Additionally, many subjects simply do not need measurement of the numerous parameters typically examined using PSG in a sleep laboratory in order to be effectively tested or diagnosed for a sleep disorder.

In addition, one important parameter to monitor during sleep disorder screening or diagnosis is a subject's respiration. One common method of monitoring a subject's respiratory effort and/or respiration volume is the use of a respiratory belt. Currently, respiratory belts are used only as sensors and, as such, are generally connected to an electronic device via significant lengths of wire which cause signal degradation and can interfere with subject mobility and/or comfort. This method of connection is necessary because current sleep diagnostic and screening devices are too large to be conveniently connected directly to the respiratory belt and/or current respiratory belts are not designed to perform the task of mechanically supporting or stabilizing a data acquisition system.

To address these shortcomings, a variety of sleep testing systems have been developed. However, many of these have been of limited portability, difficult for an untrained user to effectively utilize, and limited in their ability to record data.

It is therefore an object of the present invention to provide a compact, highly portable, user-friendly sleep disorder diagnosis and screening device. It is still another object of the present invention to provide a respiratory belt capable not only of serving as a respiratory sensor, but also of mechanically supporting and effectively securing a sleep data acquisition unit to a subject during sleep testing, allowing for greater mobility and comfort to the subject and also providing greater overall portability of the sleep diagnosis and screening system. It is still another object of the present invention to provide a compact, highly portable, user-friendly sleep disorder diagnosis and screening device which can effectively screen for/diagnose the presence of sleep apnea in a subject.

SUMMARY OF THE INVENTION

The present invention pertains to a device for conducting sleep disorder diagnosis and screening and sleep testing and analysis by measurement and collection of various physiologic data from a subject while the subject sleeps. The present invention is particularly useful in the screening and diagnosis of obstructive sleep apnea, but could also be used in diagnosis and screening of other respiratory-related sleep disorders such as central sleep apneas or primary snoring. Further, because the present invention is compact, highly portable and user-friendly, it is particularly suited for use in sleep testing at locations remote from a sleep laboratory, such as a subject's home.

The device of the present invention comprises two primary components with various other sensors associated therewith and attached thereto.

The first primary component of the present invention is a respiratory belt. For purposes of this invention, respiratory belt, or belt, can mean any device which encircles a subject's abdomen or thorax and can be used to measure certain parameters of a subject's respiration. By way of example, some common methods of performing this function involve the use of belts which measure respiration using piezoelectric crystals, impedance and inductance. Thus, the belt can take many different forms, however, in one preferred embodiment, the belt comprises an elastic substrate with conductors (e.g. wires) extending along the length of the belt, positioned in or on the elastic substrate and oriented in a sinusoidal pattern. In addition to allowing the belt to act as a respiratory sensor, the elastic substrate and the sinusoidal orientation of the conductors also allow the belt to stretch when worn by an individual and further keep the belt snugly positioned about an individual's abdomen or thorax when in use. Preferably, the belt also includes electrical connectors located at a common, single end of the belt which provide an electrical connection between the conductors positioned in or on the elastic substrate of the belt and an external device. During use, the belt is worn by a subject around the subject's abdomen or thorax and an electrical current is applied to the conductors within the belt. As the subject breathes and the belt is stretched and then relaxed, changes in inductance of the conductors occurs, allowing direct and indirect measurement of respiratory parameters such as respiratory effort or inspiratory and expiratory volumes.

Additionally, the respiratory belt in the present invention is preferably constructed so that it can effectively serve as an apparatus to mechanically support and position the data acquisition unit of the present invention which is discussed in greater detail below. This mechanical support of the data acquisition unit by the belt is a significant feature of the present invention in that it allows the data acquisition unit to be positioned on the subject in such a way that the use of long lengths of wire to connect the belt to the data acquisition unit is eliminated. This also provides greater ease of use by the subject and greater mobility and comfort for the subject while using the device. In addition, in certain embodiments, the belt may also be constructed so that the electrical connectors of the belt serve both as a point of electrical and mechanical connection between the belt and the data acquisition unit.

The second primary component of the present invention is a compact data acquisition unit which attaches to the respiratory belt just described. The data acquisition unit can take many forms; however, by way of general example, the data acquisition unit will typically include various electronic components for recording, measuring, conditioning and/or processing signals from various sensors. The data acquisition unit also typically includes a power source, such as a dry-cell battery, used to provide power to the various electronic components of the device as well as sensors used with the device.

In one embodiment of the present invention, the data acquisition unit includes sensors and connection points for sensors for measuring respiratory effort, airflow, and blood oxygenation. In this embodiment, respiratory effort could be measured using a respiratory inductance plethysmography belt, airflow could be measured using a nasal cannula connected to a pressure transducer located within the housing of the data acquisition unit and blood oxygenation could be measured using a pulse oximeter sensor attached to a subject's finger and electrically connected to the data acquisition unit. During use of the invention as envisioned in this embodiment, a subject may first position the respiratory inductance plethysmography belt around his or her thorax so that it fits snugly and both stretches and relaxes while the subject breathes. The data acquisition unit could then be both mechanically and electrically attached to the belt, allowing the belt to serve to mechanically stabilize and position the device on the subject as well as provide measurement of the subject's respiratory effort. Alternatively, the data acquisition unit could be first attached to the belt, then both the belt and data acquisition unit could be attached to the subject in a single step. Electrical current is applied to the conductors of the respiratory inductance plethysmography belt using the power source of the data acquisition unit in order to measure respiratory effort. A nasal cannula, used in measuring the subject's airflow is then attached to the data acquisition unit and worn by the subject. Finally, a pulse oximeter sensor, powered by the same power source as the data acquisition unit, is connected to the data acquisition unit and worn on the subject's finger, earlobe, or other location suitable for performing pulse oximetry. Data is then recorded by the device while the subject sleeps. Specifically, when using the device to screen for OSA, the data is recorded and then examined for periods of airflow cessation in combination with continued respiratory effort and decreased blood oxygen saturation levels to check for the presence of OSA.

In another embodiment of the present invention, the data acquisition unit may include or be used in combination with sensors in addition to those just described. For example, the data acquisition unit may further include an accelerometer for measuring a subject's posture or movement, a nasal thermistor for indirectly measuring airflow, a photodetector for measuring light levels, sound detectors for measuring various sounds including breathing sounds, various chemical or gas sensors (e.g. to measure carbon dioxide expiration), electrodes for measuring electrocardiogram, electromyogram, electroretinogram, electrooculogram, or any other sensor which is electrically based which can be used to acquire physiologically relevant data.

In still other embodiments of the present invention, the respiratory belt and/or the data acquisition unit have specifically positioned mechanical connectors for mechanically connecting the two objects to one another. These connectors can be positioned solely on either the belt or the data acquisition unit or can be a combination of complementary connectors placed individually on the respiratory belt and the data acquisition unit. One example of a mechanical connector positioned solely on the data acquisition unit is the use of a clamp attached to the back of the data acquisition unit which is used to clamp the data acquisition unit to the respiratory belt. Still other methods of mechanical attachment of the two objects can easily be envisioned by those of ordinary skill in the art such as the use of various types of fasteners and those methods are intended to be included within the scope of the present invention.

In still another embodiment of the present invention, the respiratory belt and the data acquisition unit have complementary connectors for electrical connection of the two objects. These connectors can be any type commonly known in the art. Significantly, in certain embodiments, these connectors can also serve as electromechanical connectors, providing both electrical and mechanical connection between the two objects. In still another embodiment of the present invention, the complementary connectors of the belt and the data acquisition unit may have a specific spatial orientation, such as being skewed or otherwise oriented so that the connectors are "keyed" to one another in a manner that allows attachment of the data acquisition unit to the respiratory belt in only one orientation. This approach increases measurement accuracy and ensures proper placement and orientation of the data acquisition unit on the body of the subject. Further, this approach increases the ease with which the device can be used by an untrained subject. It is to be understood that the foregoing summary and general description and the following detailed description and accompanying figures are merely exemplary of the invention, and are intended to provide an overview or framework for understanding the nature and character of the invention as it is claimed.

BRIEF DESCRIPTION OF THE FIGURES

FIG. 4 Various perspective drawings of another embodiment of the compact data acquisition unit of the present invention.

DESCRIPTION OF THE PREFERRED EMBODIMENTS

Figure 1:
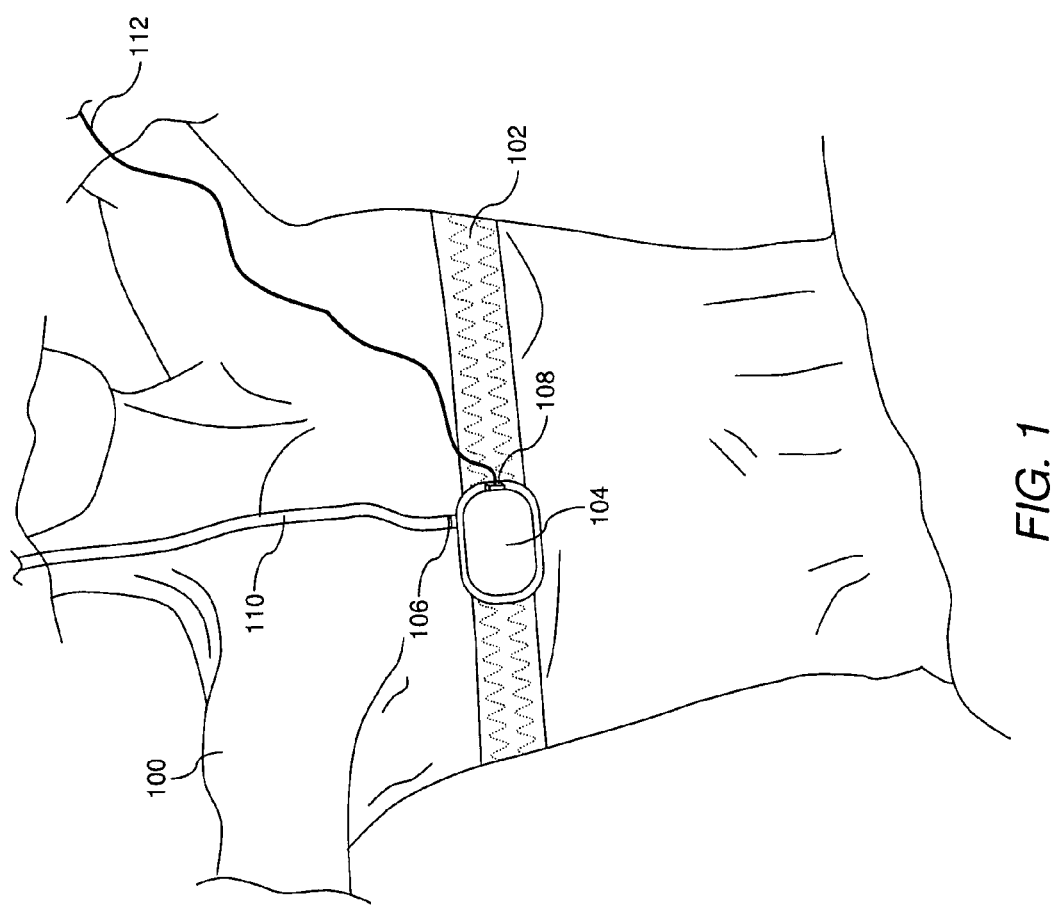
FIG. 1 Schematic showing the various components of the device as they would be applied to a subject during regular use.

The present invention is related to a device for measuring certain physiologic parameters related to a subject's sleep health while a subject sleeps. More particularly, the present invention is related to the use of a respiratory belt capable of mechanically securing and stabilizing a data acquisition unit to a subject, and further includes the use of a compact data acquisition unit to process, measure, collect and/or record physiologic data while a subject sleeps. Various embodiments of the present invention are described in greater detail below.

Various embodiments of the present invention include the use of a respiratory belt to measure various parameters of a subject's respiration, including, but not limited to, respiratory effort or changes in respiratory volume. For purposes of this invention, respiratory belt, or belt, can mean any device which encircles a subject's abdomen and can be used to measure certain parameters of a subject's respiration. By way of example, some common methods of performing this function involve the use of belts which measure respiration using piezoelectric crystals, impedance and inductance. In general use, a respiratory belt is worn around either the abdomen or thorax or both the abdomen and thorax of a subject and functions by converting the expansion of the chest or abdomen, that occurs while the subject breathes, into measurable electrical changes which provide either direct or indirect means of measurement of various respiratory parameters.

In a preferred embodiment of the present invention, the respiratory belt is a respiratory inductance plethysmography belt ("RIP" belt). The RIP belt is preferably comprised of an elastic or semi-elastic substrate with at least one conductor (e.g. a wire) positioned in or on the elastic substrate of the belt. Preferably the at least one conductor forms a continuous electrical path starting at essentially the first end of the RIP belt, going to essentially the second end of the belt and then returning back to essentially the first end of the belt such that the free ends of the conductor are positioned near a common end of the belt. The belt substrate is preferably elastic or semi-elastic so that the belt, when applied to a subject not only fits securely to the patient because of the tension created by the elastic forces, but also is able to stretch and contract in order accommodate expansion and contraction of the abdomen and/or thorax during breathing. The RIP belt may vary in length according to the application in which it is used, with shorter lengths being used for smaller subjects and longer lengths used for larger subjects. Additionally, the width and thickness of the RIP belt may vary. The conductor or at least one conductor associated with the RIP belt is preferably a wire or other long, narrow conductor which is woven or otherwise situated within the substrate of the RIP belt. By way of example, but not limitation, conductors used with the RIP belt of the present invention can include high strand count copper wire, other types of wire including solid wire made from copper or aluminum, or any other conductor commonly used in the art including various types of alloys or metals not mentioned herein. Further, in certain embodiments, the conductors may be attached only to the surface of the elastic substrate and not situated within the substrate of the belt. In order to provide effective measurement of changes in inductance and in order to allow for stretching and contraction of the RIP belt, the at least one conductor positioned in or on the RIP belt is preferably oriented in a repeating symmetrical pattern which runs the length of the belt such as a 'zigzag' or sinusoidal pattern.

The RIP belt of the present invention further includes fasteners used in attaching the belt to the subject during use of the belt. The fasteners used with the RIP belt of the present invention can be any type known or commonly used in the art including, but not limited to, adhesive-based fasteners, hook-and-loop type fasteners, or traditional buckle fasteners where one end of the belt is looped through a buckle attached at the opposite end of the belt in order to secure the belt to the patient. Preferably these fasteners are robust enough to provide a significant amount of mechanical integrity to the RIP belt so that the belt, in addition to serving as a respiratory sensor, may also serve as an apparatus for positioning and/or supporting a data acquisition unit.

For one to use changes in inductance to measure respiratory parameters, the conductors of the RIP belt must be electrically connected to an external device capable of generating and passing an electrical current through the conductor(s) positioned in or on the elastic substrate of the RIP belt. One preferable method of providing an electrical connection between conductors located within the substrate of the RIP belt and an external device is the use of metal button-snap connectors which are permanently attached to the RIP belt substrate in such a manner that the connectors contact the conductors and provide electrical connection between the conductors and an external device. It will be clear to one of ordinary skill in the art that various other types of standard electrical connectors could be substituted for the metal button-snap connectors just described without changing the nature or scope of the invention. Still other methods exist for providing a connection between the conductors situated within the substrate of the RIP belt and an external device, including the use of insulation penetrating and displacement methods. For example, tapered, conductive points, which are electrically attached to an external device, could be passed through the RIP belt substrate, displacing the substrate and contacting the conductors, thus, providing a point of electrical contact with the conductors positioned in or on the substrate of the belt. It is clear from the above examples that connection of the conductors of the belt to an external device can be accomplished in many ways and the examples provided herein are examples only and are not intended to limit the present invention.

A common feature of all embodiments of the RIP belt of the present invention is that they are preferably single-ended. By single-ended it is meant that the electrical connection(s) to the conductor(s) situated within the elastic substrate of the belt are located at a single, common end of the belt. If a single conductor is used in the RIP belt, single-endedness is achieved by running the conductor along the length of the RIP belt from one end of the belt along one edge of the belt, and upon reaching the opposite end of the belt, running the conductor back to the starting point. If two conductors are used, the conductors may be run in parallel along the length of the RIP belt. In order to achieve single-endedness when using two conductors positioned in or on the RIP belt substrate, the conductors must be electrically connected together at one end of the RIP belt. This can be accomplished in a number of ways, however, one preferable way is to attach a conductive end cap to one end of the RIP belt which serves to electrically connect the two conductors. Still more than two conductors could be used in the RIP belt if desired, and this approach could be implemented using any, or a combination of, the methods and embodiments described herein. In still other embodiments, the belt could contain multiple passes of one or multiple conductors from one end of the belt to the other end of the belt in various patterns including loops of the conductor within or on the belt substrate. Further, an additional method of achieving single-endedness could include the use of conductor disposed within or on the belt to form an electrically single continuous loop. This method would produce single-endedness through the use of a data acquisition unit designed to electrically connect to the conducting loop while at the same time forming an electrical break in the loop to allow current to pass from one end of the broken loop to the other. Such a system would have the advantage that the data acquisition unit could be attached at any location along the length of the belt. Certain other preferred embodiments of the RIP belt of the present invention are described in greater detail in the description of the figures provided below.

Various embodiments of the present invention further include a compact data acquisition unit. The data acquisition unit is preferably comprised of at least a power source, a memory module, and a processor for use in collection, storage, and analysis of data and generation of output signals. In its simplest form, the data acquisition unit can include only a single input channel for recording input from the RIP belt of the present invention. In this embodiment, the data acquisition unit used with the RIP belt serves only as a respiratory sensor. In still other embodiments the data acquisition system may have multiple inputs for multiple sensors. By way of example, but not limitation, sensors that could be included within or used in combination with the data acquisition unit include wet or dry electrodes, photodetectors, accelerometers, pneumotachometers, strain gauges, thermal sensors, pH sensors, chemical sensors, gas sensors (such as oxygen and carbon dioxide sensors), various transducers, piezo sensors, magnetometers, pressure sensors, microphones, biometric sensors and the like. In one preferred embodiment, the data acquisition unit includes inputs for recording data from three sensors including a pulse oximetry sensor, an airflow sensor (e.g. a pressure transducer located within the device housing and attached to a nasal cannula), and a RIP belt. This embodiment is preferable because it allows efficient and effective screening for, and diagnosis of, obstructive sleep apnea with a minimum number of sensors. Further, because of the limited number of sensors and the compact nature of the data acquisition unit, this embodiment lends itself particularly to portable, in-home sleep testing. Still other embodiments can be envisioned wherein the data acquisition unit includes other sensors in addition to the three just mentioned, such as a thermistor for measuring temperature or breathing rate or an accelerometer for measuring movement and/or orientation during sleep screening/diagnosis.

During use, the data acquisition unit is preferably attached to the RIP belt of the present invention and the RIP belt, in addition to acting as a respiratory sensor, is used to secure the data acquisition unit to the subject and to provide mechanical support to the data acquisition unit. Attachment of the data acquisition unit to the RIP belt can be accomplished in a number of ways including, but not limited to, the use of complementary electrical connectors, adhesives, hook-and-loop fasteners, belt loops or clamps, and any other method commonly known in the art and suitable to such application. In addition, the data acquisition unit may be constructed in such a way as to have the RIP belt threaded through the acquisition device or to have the acquisition device clamp over the belt. One preferred method of attaching the data acquisition unit to the RIP belt includes using complementary electrical connectors, such as the male and female ends of a standard button snap connector, attached respectively to the RIP belt and the data acquisition system to provide both an electrical and a mechanical connection between the RIP belt and the data acquisition system using a single method of connection. Still other embodiments involve a method of attachment which uses both complementary electrical connectors as well as hook-and-loop type fasteners to secure the data acquisition unit to the single-ended RIP belt. Still other embodiments may involve the use of one or a combination of the above methods of attachment in conjunction with the use of specific spatial orientation of the fasteners and/or connectors, such as orienting the fasteners and/or connectors in a skewed manner on the respiratory belt and data acquisition device so that the fasteners and/or connectors on the belt are "keyed" to the fasteners and/or connectors on the data acquisition unit, or vice versa. Using a "keyed" method of attachment helps ensure that the data acquisition unit is properly attached to the belt and increases ease of use of the device as well as reliability of measurements obtained using the device. It will be apparent to those skilled in the art that still many other methods and combinations of methods exist for attaching the data acquisition unit of the present invention to the single-ended RIP belt of the present invention, and those examples given above are given by way of illustration only and not by limitation.

In still another embodiment, it may be desirable to use the data acquisition unit of the present invention with two RIP belts in order to better ascertain a subject's breathing effort and/or behavior, such as when one is monitoring the subject for paradoxical breathing. In this embodiment, two separate RIP belts are placed on the subject with a first belt placed around the subject's thorax and a second belt placed around the subject's abdomen. In this embodiment, the data acquisition unit of the present invention could include two channels for recording respiratory effort. The first channel could be connected to the RIP belt positioned around the subject's thorax as just described, with this belt serving to position and mechanically support the data acquisition unit. The second belt could then be connected to the device using a wired electrical extension reaching from the second belt and connecting to the data acquisition unit using a releasable electrical connector or other similar means of connection.

It will be clear to those of ordinary skill in the art that many other embodiments beyond those examples disclosed above exist within the scope of the present invention.

Turning now to a description of the figures, FIG. 1 shows the various components of one embodiment of the present invention as they would be applied to a subject 100 during regular use. Among the components of the present invention shown in FIG. 1 are a single-ended respiratory inductance plethysmography belt 102 and a compact data acquisition unit 104. The data acquisition unit 104 further includes a point of connection to a nasal cannula 106 for use in measuring airflow, and a point of connection to a pulse oximeter 108 for measuring heart rate and blood oxygenation. Here, in addition to providing data pertaining to the subject's respiration, the respiratory belt 102 is used to mechanically support the data acquisition unit 104 and attach the data acquisition unit 104 to the subject 100. The means of mechanical and electrical connection of the data acquisition unit to the belt are not shown. When worn by the subject 100 during sleep, the various components, serve to diagnose or assess the subject's likelihood of having a sleep disorder by measuring respiratory effort, airflow, and blood oxygen saturation while the subject sleeps. Also shown in FIG. 1 are the hose for connection of a nasal cannula 110 to the data acquisition unit 104, and a wired electronic connection 112 from the data acquisition unit 104 to a pulse oximeter (not shown).

Figure 2:
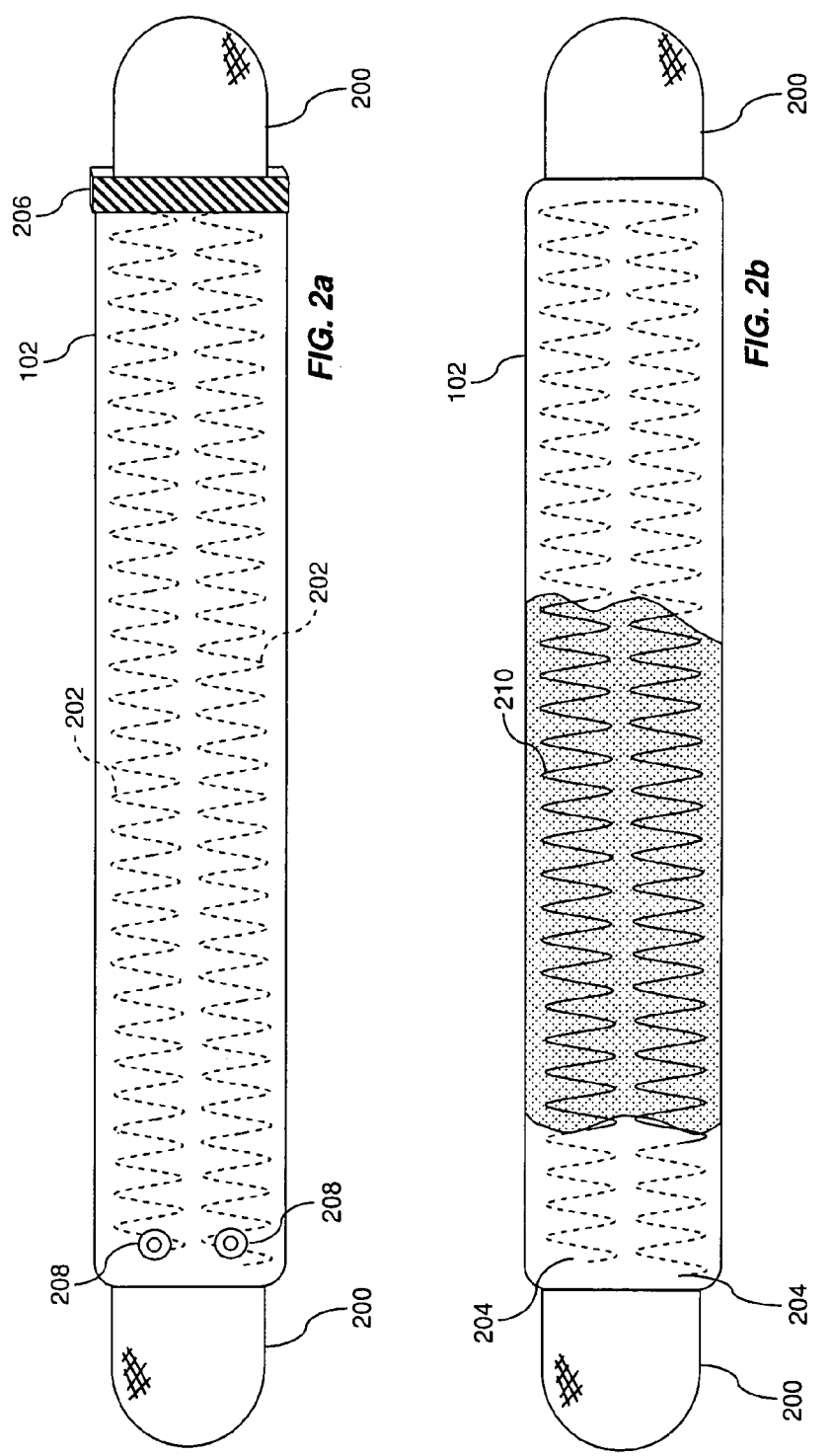
FIG. 2 Two exemplary embodiments of a respiratory inductance plethysmography belt used in the present invention.

FIG. 2 shows, in greater detail, the single-ended respiratory inductance plethysmography belt 102 of FIG. 1. The single-ended respiratory inductance plethysmography belt 102 is referred to as being "single-ended" because in certain preferable embodiments such as those shown in FIG. 2, the points of electrical connection 208, 204 to the conductors 202, 210 in the belt are located at a common, single end of the belt 102. As depicted here, the single-ended respiratory inductance plethysmography belt 102 includes fasteners 200 at each end for use in attaching the belt around a subject. However, fasteners 200 need not be located at each end of the belt and there are various other embodiments in which a single fastener used at only one end of the belt may be applied. Further, the fasteners 200 can be any type known or commonly used in the art including, but not limited to, adhesive-based fasteners, hook-and-loop type fasteners, button-type fasteners, traditional buckle fasteners where one end of the belt is looped through a buckle attached at the opposite end of the belt in order to secure the belt around the subject, and the like.

The single-ended respiratory inductance plethysmography belt 102 itself is preferably composed of an elastic or partially elastic substrate with conductors 202, 210 disposed in or on the elastic substrate. The elasticity allows the belt to fit securely around a range of subjects. Although conductors 202, 210 are shown disposed within the elastic substrate in FIG. 2a and FIG. 2b, they could just as easily be attached to the surface of the elastic substrate, laminated between substrates, or coated or printed on the substrate, and the two examples shown in FIG. 2 are not intended to limit the scope of the present invention. Further, although the conductors are shown in FIG. 2a and FIG. 2b attached to the elastic substrate in a zigzag pattern, they could just as easily be attached using any other geometric layout (e.g. a sinusoidal pattern) which allows for measurement of inductance changes as described below and also allows for changes in length of the belt. During use, the single-ended respiratory inductance plethysmography belt is secured around the thorax or abdomen of a subject using the fasteners 200 and an electrical current is passed through the conductors 202, 210. This electrical current will generally be supplied by the data acquisition unit, which is preferably capable of controlling the amount of current, and the amplitude and frequency of the current applied to the conductors 202, 210 of the belt. Passing an electrical current through the conductors causes a magnetic field to be generated around the conductors. Conversely, changes in this magnetic field lead to changes in current flow through the conductor. Thus, as a subject breathes and the cross-sectional area of the subject's thorax or abdomen changes, the single-ended respiratory inductance plethysmography belt 102 stretches or contracts causing adjacent zigzagging segments of the conductors 202, 210 to move closer to, or farther away from, one another leading to an interaction between the magnetic fields surrounding the adjacent zigzagging segments of the conductors, which, in turn, yields a measurable change in overall inductance. This change in inductance is then used to directly or indirectly measure certain parameters of a subject's respiration such as respiratory effort, or changes in volume of the abdomen or thorax.

FIG. 2a shows one embodiment of the single-ended respiratory inductance plethysmography belt 102 of the present invention wherein electrical connectors 208 are permanently attached to the belt, providing an electrical connection through the elastic substrate of the belt to each of the conductors 202 embedded therein. The electrical connectors 208 allow electrical connection of the conductors 202 to external devices such as the data acquisition unit 104 shown in FIG. 1 and described in greater detail below. As noted above, it is preferable that the electrical connectors 208 are both located at a single end of the belt 102 as shown in FIG. 2a to increase the ease with which the belt 102 can be attached to, and used with, external devices such as the data acquisition unit 104 as illustrated in FIG. 1. Although the electrical connectors 208 are shown in FIG. 2a as being aligned along a common vertical axis, they could just as easily be positioned in any other spatial orientation at a common end of the belt. For example, the electrical connectors 208 could be positioned such a way as would allow the belt 102 and the data acquisition unit 104 to be "keyed" to one another (e.g. so that they neither a vertical nor a horizontal axis). A "keyed" orientation such as this would increase ease of use by untrained subjects as well as improve data reliability by ensuring proper orientation of the data acquisition unit and the belt when the device is used by a subject. The embodiment shown in FIG. 2a further shows a conductive end cap 206 attached to one end of the belt and used to electrically connect the two conductors 202 to one another. The use of such an end cap is advantageous in that it provides greater ease and efficiency when manufacturing the belt, since the belt can be produced as a continuous linear piece and then cut to any length desired and the end cap added in order to connect the two conductors to one another and thus allow placement of the electrical connectors 208 at a single end of the respiratory inductance plethysmography belt.

FIG. 2b shows another embodiment of the single-ended respiratory inductance plethysmography belt 102 of the present invention wherein a single conductor 210 is disposed within the belt 102 and oriented in such a way that the conductor 210 extends along the length of the belt 102 and the free ends 204 of the conductor 210 are positioned at a common end of the belt. Because the embodiment shown in FIG. 2b lacks permanent electrical connectors 208 shown in FIG. 2a, electrical connection to the conductor 210 must be made by penetration or displacement of the elastic substrate. This can be accomplished various ways, however, one preferable approach is to have conductive insulation displacement barbs, or points attached, for example, to a data acquisition unit. When the device is used with the single-ended respiratory inductance plethysmography belt shown in FIG. 2b, the conductive insulation displacement barbs or points can be used to penetrate the elastic substrate of the belt and electrically connect the data acquisition unit to the conductor 210 located within the belt, allowing measurement of respiratory effort or change in abdominal or thoracic volume using inductance changes as described above.

Additionally, the single-ended respiratory inductance plethysmography belt may include exposed or uninsulated conductors, which conductive areas on the data acquisition unit may contact in order to establish an electrical connection between the conductors in or on the single-ended respiratory inductance plethysmography belt and the data acquisition unit. In this embodiment, two isolated conductive contact plates could be placed on the outside of the data acquisition unit and positioned so that each plate contacts a single conductor or single end of an uninsulated conductor disposed in or on the belt. The data acquisition unit could then be attached to the single-ended respiratory inductance plethysmography belt in such a way that a force is present which maintains electrical connection between the contact plates of the data acquisition unit and the conductors of the belt. For example, the data acquisition unit could be clamped onto the belt in such a way as to maintain electrical connection between the conductive contact plates of the data acquisition unit and the conductors of the single-ended respiratory inductance plethysmography belt.

It is further significant that in both FIG. 2a and FIG. 2b the single-ended respiratory inductance plethysmography belt 102, during use, functions both as a sensor and as a means of mechanically stabilizing and supporting a data acquisition unit. Additionally, in embodiments such as the one shown in FIG. 2a, the electrical connectors 208 can serve simultaneously as both points of electrical connection and points of mechanical connection and support to an external device.

It is clear that there are many ways not described herein in which one could combine the various elements of the exemplary embodiments shown in FIG. 2 and combination of the various features of the embodiments shown in FIG. 2 is intended to be included within the scope of the present invention.

Figure 3:
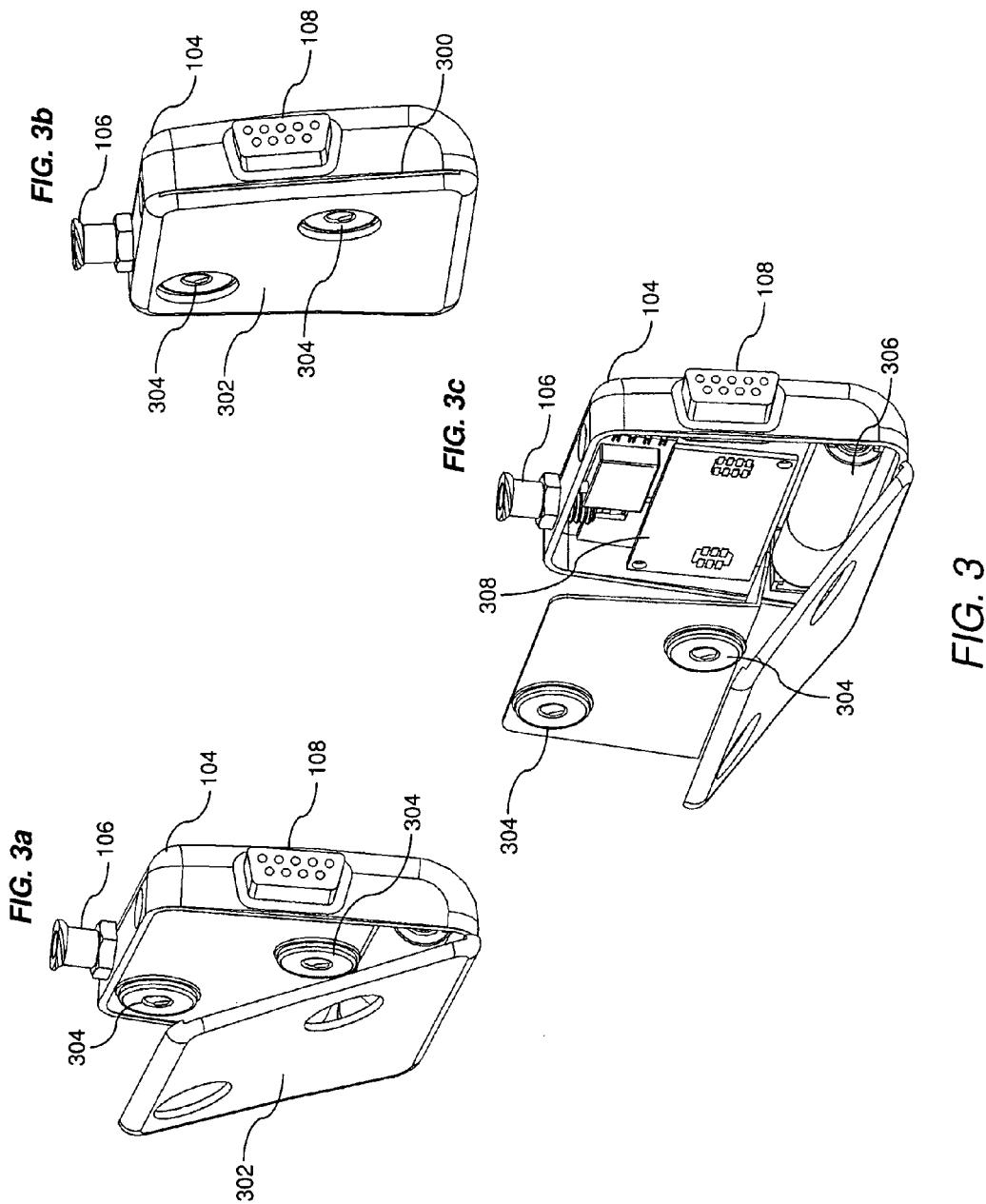
FIG. 3 Various perspective drawings showing the features of one embodiment of the compact data acquisition unit of the present invention.

FIG. 3 shows various perspective views of one embodiment of the data acquisition unit 104 of the present invention. As previously shown in FIG. 1, the embodiment shown in FIG. 3 includes a point of connection to a nasal cannula 106 for measuring airflow, and a point of connection to a pulse oximeter 108 for measuring heart rate and blood oxygenation. As shown in FIG. 3c, the data acquisition unit further includes various electronic components 308 used to perform signal output, data storage, and processing and/or acquisition of data. Preferably, these electronic components are capable of providing a wide range of outputs and accepting a wide range of inputs, so as to allow more detailed analysis of various measurements obtained using the device. A power source 306 in the form of a dry-cell battery is also illustrated in FIG. 3c as a means of providing power to the various electronic components 308. Although the power source 306 shown in FIG. 3c is a standard dry cell type battery, other power sources could be used including, but not limited to, large capacitors, other types of batteries, or powering through a USB connection, voltage adapter, A/C or D/C adapter or the like. Further, the data acquisition unit 104 need not necessarily be limited to receiving power from a single power source. For example, in one preferred embodiment a battery-based power source may be removed in order to facilitate connection of the data acquisition unit 104 to a computer and subsequent download of recorded data to the computer for further analysis. In this embodiment, a USB connection is made between the computer receiving the data and the data acquisition unit 104, and the USB connection is used to power the data acquisition unit 104 during this time. In still other embodiments, an internal power-sustaining device such as a coin battery or large capacitor may be used to maintain power to an internal clock to ensure proper real time recording in cases in which the data acquisition unit 104 does not receive power from other sources such as a USB connection or a dry cell battery. The embodiment shown in FIG. 3 also includes a hinged back panel 302 and electrical connectors 304 for connection of the data acquisition unit to a respiratory belt. Although the electrical connectors shown in FIG. 3 are button-snap type connectors, they could just as easily be any other type of electrical connector commonly used in the art. The hinged back panel 302 is shown in the open position in FIG. 3a and in the closed position in FIG. 3b. As can be seen from FIG. 3b, when the hinged back panel 302 is in the closed position, space exists 300 between the main body of the data acquisition unit and the hinged back panel, providing room for placement of a respiratory belt between the hinged back panel and the main body of the data acquisition unit.

In one envisioned application of the embodiment shown in FIG. 3, a respiratory belt, equipped with electrical connectors complementary to those on the data acquisition unit, is passed between the main body of the data acquisition unit and the hinged back panel 302 and connected to the electrical connectors of the data acquisition unit 304. After electrical connection of the respiratory belt with the data acquisition unit, the hinged back panel 302 of the device is closed over the belt, providing a means of mechanical attachment of the device to the belt.

Referring now to FIG. 4, there are shown two perspective views of another embodiment of the data acquisition unit 104 of the present invention. FIG. 4a shows a perspective view of the front of the device of this embodiment, while FIG. 4b shows a perspective view of the back of the device. Both FIG. 4a and FIG. 4b include features of the data acquisition unit previously discussed, including a point of connection to a nasal cannula 106, a point of connection to a pulse oximeter 108, and points of electrical connection to a respiratory belt 304. In addition to those features already discussed, the embodiment shown in FIG. 4 further includes a point of connection to a nasal temperature probe, or thermistor 400 for use in indirectly measuring airflow and/or measuring breathing rate using temperature fluctuations that occur when a subject breathes. The embodiment of the data acquisition unit shown in FIG. 4 differs from the embodiment shown in FIG. 3 in that it does not include a hinged back panel 302 to provide a mechanical connection between the data acquisition unit 104 and a respiratory belt. Rather, in this embodiment, both a mechanical and an electrical connection to the respiratory belt are provided by the electrical connectors 304. Thus, in this embodiment, not only do the electrical connectors 304 provide a means of electrical connection to a respiratory belt, but they also provide a means of mechanical connection to the belt, allowing the belt to provide both respiratory sensing capabilities and mechanical support to position the data acquisition unit 104 on a subject using only a single type of connector.

The embodiment of the data acquisition unit shown in FIG. 4a further shows a flat area 402 located on the front of the data acquisition device 104. This flat area 402 preferably is used as an area within which various indicators or switches are positioned to control the data acquisition unit and communicate with the user. In one preferred embodiment, this area may include a power switch as well as various light emitting diodes (LEDs) which can be used to indicate whether sensors are properly attached to the device and/or properly recording data. For example, if the data acquisition unit 104 senses that a sensor is not working properly, an indicator comprised of an LED may be lit in order to communicate to the user that the sensor is functioning improperly or is in need of replacement. Still other indicators may be used for other purposes such as indicating level of battery life or indicating whether or not data is being recorded.

It will be apparent to those skilled in the art that various modifications and variations can be made to the present invention as described above without departing from the spirit and scope of the invention. Thus, it is intended that the present invention cover the modifications and variations of this invention provided they come within the scope of the appended claims and their equivalents.

What we claim is:

1. A sleep diagnostic and screening device comprising
a data acquisition unit, the data acquisition unit comprising:
   a power source, the power source for providing power to the data acquisition unit and for providing power to sensors connected to the data acquisition unit;
   at least three input channels having at least two input connectors and a point of connection for a nasal cannula; and
   at least one electronic component for collecting and storing data;
a respiratory belt having two ends comprising fasteners at each end adapted to attaching the belt around a subject, and an electronic connector for electronically connecting the data acquisition unit directly to the respiratory belt without the use of a length of wire, the electronic connector being oriented on the respiratory belt in such a way that the data acquisition unit can be connected to the respiratory belt in only one orientation;
a nasal cannula for measuring airflow; and
a pulse oximeter comprising an input connector for electronically connecting the data acquisition unit to the pulse oximeter.

2. The sleep diagnostic and screening device of claim 1 wherein the data acquisition unit further includes an input channel and an input connector for connecting a thermistor, and the sleep diagnostic and screening device further includes a thermistor.

3. The sleep diagnostic and screening device of claim 1 wherein the respiratory belt is a single-ended respiratory belt, the belt having two ends.

4. The sleep diagnostic and screening device of claim 1 wherein the data acquisition unit further includes an accelerometer, internal to the data acquisition unit, for measuring subject movement and/or position.

5. The sleep diagnostic and screening device of claim 1 wherein the respiratory belt comprises button snap connectors and all of a plurality of the respiratory belt button snap connectors make both an electrical connection and at least a partial mechanical connection of the data acquisition unit to the respiratory belt.

6. The sleep diagnostic and screening device of claim 3 wherein the single-ended respiratory belt is a respiratory inductance plethysmography belt comprising a single conductor having free ends and oriented in such a way that the conductor extends along a length of the belt and the free ends of the conductor are positioned at a common end of the belt.

* * * * *